United States Patent
Dilmaghanian

(10) Patent No.: US 9,682,242 B2
(45) Date of Patent: Jun. 20, 2017

(54) CONNECTOR WITH LOW LEAD INSERTION FORCE AND METHOD OF REDUCING SAME

(75) Inventor: Farshid Dilmaghanian, Foothill Ranch, CA (US)

(73) Assignee: Bal Seal Engineering, Inc., Foothill Ranch, CA (US)

( * ) Notice: Subject to any disclaimer, the term of this patent is extended or adjusted under 35 U.S.C. 154(b) by 801 days.

(21) Appl. No.: 12/618,493

(22) Filed: Nov. 13, 2009

(65) Prior Publication Data
US 2010/0123291 A1    May 20, 2010

Related U.S. Application Data

(60) Provisional application No. 61/114,915, filed on Nov. 14, 2008.

(51) Int. Cl.
| | |
|---|---|
| *A61N 1/37* | (2006.01) |
| *H01R 24/58* | (2011.01) |
| *H01R 13/52* | (2006.01) |
| *F16J 15/02* | (2006.01) |
| *A61N 1/375* | (2006.01) |

(52) U.S. Cl.
CPC .......... *A61N 1/3752* (2013.01); *F16J 15/025* (2013.01); *H01R 13/5224* (2013.01); *H01R 24/58* (2013.01); *F16J 15/024* (2013.01); *H01R 13/521* (2013.01); *H01R 2201/12* (2013.01)

(58) Field of Classification Search
CPC .. A61N 1/3752; H01R 2201/12; H01R 24/58; H01R 13/521; H01R 13/5224; F16J 15/024; F16J 15/025
USPC ....... 277/551, 630, 641, 616, 626, 637, 643, 277/644; 607/37
See application file for complete search history.

(56) References Cited

U.S. PATENT DOCUMENTS

| | | | | |
|---|---|---|---|---|
| 2,995,057 | A | * | 8/1961 | Nenzell .......................... 411/399 |
| 4,311,248 | A | * | 1/1982 | Westerlund et al. .......... 277/626 |
| 4,616,857 | A | * | 10/1986 | Woodman et al. ......... 285/123.3 |
| 5,261,395 | A | * | 11/1993 | Oleen et al. ..................... 607/15 |
| 5,413,595 | A | | 5/1995 | Stutz, Jr. |
| 5,669,790 | A | * | 9/1997 | Carson et al. ................. 439/668 |
| 5,720,631 | A | * | 2/1998 | Carson et al. ................. 439/668 |
| 6,029,089 | A | * | 2/2000 | Hawkins et al. ................ 607/37 |
| 6,089,543 | A | * | 7/2000 | Freerks .......................... 251/357 |
| 6,173,969 | B1 | * | 1/2001 | Stoll et al. ..................... 277/630 |
| 6,305,695 | B1 | * | 10/2001 | Wilson .......................... 277/584 |

(Continued)

FOREIGN PATENT DOCUMENTS

WO    WO 03/075414 A1    9/2003

OTHER PUBLICATIONS

International Perliminary Report on Patentability mailed May 26, 2011 from corresponding International Application No. PCT/US2009/064527, filed Nov. 16, 2009 (8 pages).

(Continued)

*Primary Examiner* — Nicholas L Foster
(74) *Attorney, Agent, or Firm* — Klein, O'Neill & Singh, LLP

(57) ABSTRACT

Aspects of the disclosed embodiments are directed toward specialized seals necessary between electrical connectors as used in Implantable Pulse Generators (IPG's) and other implantable connectors, the seals comprising a seal lip and undercuts in an interior wall surface to increase a length to width ratio of the seal lip to at least 2:1.

18 Claims, 3 Drawing Sheets

(56) References Cited

U.S. PATENT DOCUMENTS

| | | | | |
|---|---|---|---|---|
| 6,390,843 | B1* | 5/2002 | Lim | 439/346 |
| 6,536,775 | B1* | 3/2003 | Inciong | 277/596 |
| 6,895,276 | B2* | 5/2005 | Kast et al. | 607/37 |
| 7,048,279 | B2* | 5/2006 | Gernand et al. | 277/596 |
| 7,083,474 | B1* | 8/2006 | Fleck et al. | 439/668 |
| 7,159,874 | B2* | 1/2007 | Hosokawa | 277/651 |
| 7,164,951 | B2* | 1/2007 | Ries et al. | 607/37 |
| 7,282,097 | B2* | 10/2007 | Tanase et al. | 118/733 |
| 7,404,884 | B2* | 7/2008 | Montminy et al. | 204/632 |
| 7,413,164 | B2* | 8/2008 | Yamagishi | 251/333 |
| 7,526,339 | B2* | 4/2009 | Lahti et al. | 607/37 |
| 7,647,111 | B2* | 1/2010 | Ries et al. | 607/37 |
| 7,717,754 | B2* | 5/2010 | Ries et al. | 439/669 |
| 2004/0034393 | A1* | 2/2004 | Hansen et al. | 607/37 |
| 2007/0225772 | A1 | 9/2007 | Lahti et al. | |
| 2008/0246231 | A1* | 10/2008 | Sjostedt et al. | 277/641 |
| 2011/0059639 | A1* | 3/2011 | Dilmaghanian et al. | 439/271 |

OTHER PUBLICATIONS

International Search Report completed Jul. 5, 2010 and mailed Jul. 6, 2010 from corresponding International Application No. PCT/US2009/064527, filed Nov. 16, 2009 (3 pages).

Written Opinion completed Jul. 5, 2010 and mailed Jul. 6, 2010 from corresponding International Application No. PCT/US2009/064527, filed Nov. 16, 2009 (4 pages).

* cited by examiner

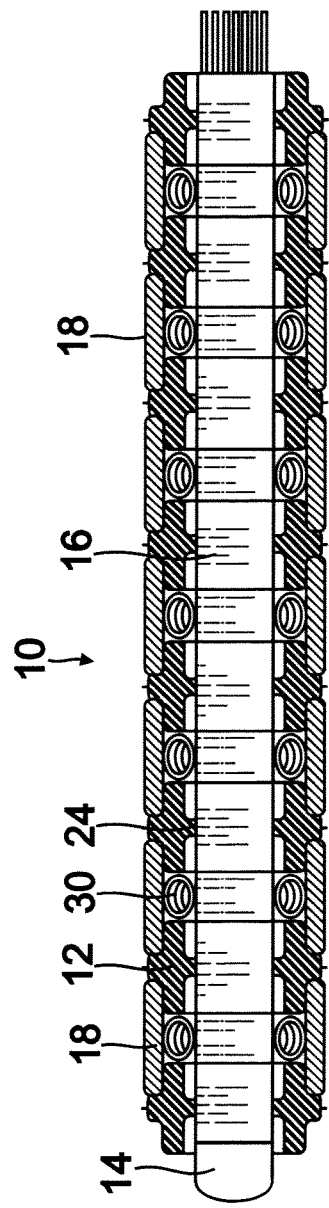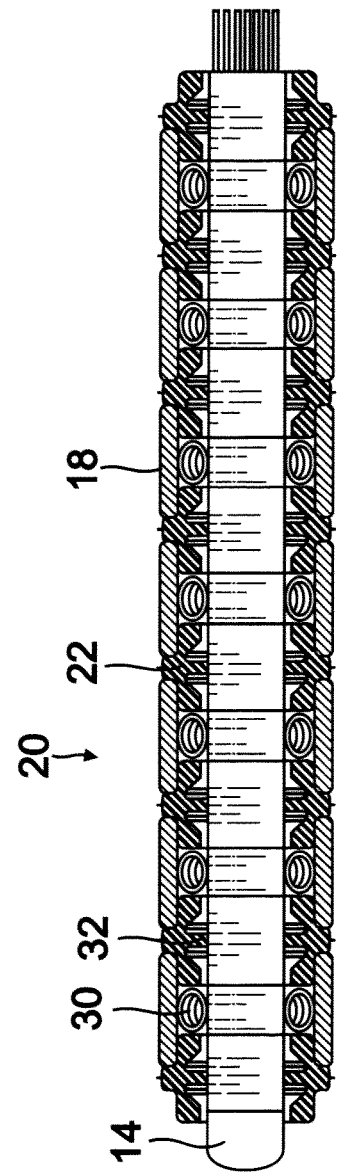

US 9,682,242 B2

CONNECTOR WITH LOW LEAD INSERTION FORCE AND METHOD OF REDUCING SAME

CROSS-REFERENCE TO RELATED APPLICATION

This is a regular application of provisional application No. 61/114,915, filed Nov. 14, 2008; the contents of which are expressly incorporated herein by reference as if set forth in full.

BACKGROUND

Implantable medical devices, such as Implantable Pulse Generators (IPG's) used in implantable Cardiac Rhythm Stimulator (CRM) devices and Neurostimulator devices, typically have connector contacts that establish electrical connection between the IPG and the lead which directs the stimulus to the target area in the body. A plurality of connector contacts as used in both CRM and Neurostimulator devices range from 3 to 7 contacts that are stacked in-line. The contacts must be separated electrically by a dielectric insulator seal. The seal must also prevent the migration of body fluids between the electrical contacts of the IPG. Another desirable characteristic of the seals and possibly the contacts is adequate sealing force around the lead to maintain body fluid sealing to the lead while still providing acceptable insertion force. Exemplary IPGs and in line header connectors are disclosed in Ser. No. 11/839,103, filed Aug. 15, 2007, entitled Connector Assembly for Use with Medical Devices; Ser. No. 12/062,895, filed Apr. 4, 2008, entitled Connector Assembly for Use with Medical Devices; and Ser. No. 12/100,646, filed Apr. 10, 2008, entitled Integrated Header Connector System, the contents of each of which are expressly incorporated herein by reference.

The process of implanting an IPG of the CRM or Neurostimulator type typically requires a doctor to insert the stimulator lead into the IPG header containing a plurality of in-line contacts and seals. A typical commercially available lead is flexible by nature because it is made up of alternating metallic contact rings and separating dielectric spacers between the contact rings. Additionally, the lead is typically about 0.050 inches in diameter, which miniature size adds to its flexibility. It is therefore desirable to provide a device in which the force to insert the lead into the IPG header with its contacts and seals be appropriate for a miniature size lead. It is also desirable to formulate a method for reducing insertion force between a lead and an in line header connector. If the insertion force is too high, the lead may buckle and become difficult if not impossible to insert into the header assembly of the IPG. The need for low insertion force and adequate sealing therefore becomes even more important on modern neurostimulators where seven (7) or more alternating contacts and seals are used in line or as an integrated stack for each lead. In general, it is desirable to have an in-line connector as shown and described and/or to have systems and methods for using the same.

SUMMARY

The preferred embodiments of the present in-line connectors and related methods have several features, no single one of which is solely responsible for their desirable attributes. Without limiting the scope of the present embodiments as expressed by the claims that follow, their more prominent features now will be discussed briefly. After considering this discussion, and particularly after reading the section entitled "DETAILED DESCRIPTION", one will understand how the features of the present embodiments provide advantages, which include the ability to reduce insertion force.

One embodiment of the present apparatus includes an elastomeric seal for use in an in-line header connector between electrical contacts tailored geometrically to provide adequate sealing of body fluids, the seal comprising undercuts in an interior wall surface to increase a slenderness ratio of a seal lip to at least 2:1 length to width.

Another feature of an embodiment is an elastomeric seal for use in an in-line header connector between electrical contacts, said seal comprising a wall structured with undercuts that allows a sealing lip located between two end openings to deflect in an axial direction to allow a lead to pass with desired low insertion force.

A further aspect is understood to include a method for decreasing an insertion force of a lead into an in line header connector comprising: forming an in line header connector comprising a plurality of alternating seals and contact elements and a common bore, inserting a lead into the common bore with reduced insertion force; and wherein the inserting step comprises deflecting a plurality of seal lips axially in a direction of the insertion of the lead.

BRIEF DESCRIPTION OF THE DRAWINGS

The preferred embodiments of the present in-line connector and related methods now will be discussed in detail with an emphasis on highlighting the advantageous features. These embodiments depict the novel and non-obvious in-line connectors shown in the accompanying drawings, which are for illustrative purposes only. These drawings include the following figures, in which like numerals indicate like parts:

FIG. 1 is a cross-sectional view of an in-line connector having multiple contact rings, spring contacts, and seals and having a lead disposed in a common bore.

FIG. 2 is a cross-sectional view of an in-line connector having multiple contact rings, spring contacts, and seals and having a lead disposed in a common bore and wherein the lip seals are configured for low force insertion.

DETAIL DESCRIPTION

Figure 3:
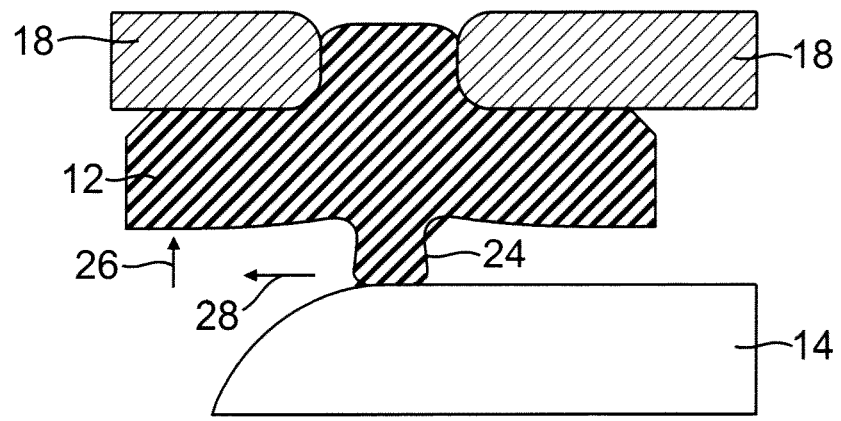
FIG. 3 is an enlarged sectional view of the connector of FIG. 1.

The detailed description set forth below in connection with the appended drawings is intended as a description of the presently preferred embodiments of an in-line connector and components thereof provided in accordance with aspects of the present invention and is not intended to represent the only forms in which the present invention may be constructed or utilized. The description sets forth the features and the steps for constructing and using the connectors and components of the present invention in connection with the illustrated embodiments. It is to be understood, however, that the same or equivalent functions and structures may be accomplished by different embodiments that are also intended to be encompassed within the spirit and scope of the invention. As denoted elsewhere herein, like element numbers are intended to indicate like or similar elements or features.

IPG seals are typically made of medical implantable grade silicone elastomer with a durometer of approximately 40 Shore D, such as that shown in FIG. 1 having element 10. An interference fit of about 0.010 inches radially is typically incorporated between the lip 24 of the seal 12 and the lead 14 in order to establish an effective seal against body fluid migration between contacts 18. In the accompanying figures, eight seals are shown each having a lip 24 abutting against the lead to seal against the perimeter of a corresponding lead insulator 16. A canted coil spring 30 is shown located in the cavity of each contact 18. In other embodiments, less than eight seals or more than eight seals are used to seal against a corresponding number of lead insulators.

With conventional radial interference, the seal lip primarily deflects in the radial direction (i.e., they compress mostly radially outwardly relative to the axis of the lead 14), which results in relatively high insertion force. As is clear to a person of ordinary skill in the art, the force is increased in a multi-seal in line connector application due to insertion force across each seal.

In accordance with aspects of the present in-line connector 20, the seal 22 cross section is undercut or relieved to increase the length of the seal lip thus allowing it to deflect axially relative to the lead versus radially which results in lower insertion force. The cut back or relief in the seal cross section changes the seal performance by allowing the longer length lip to deflect to achieve the desired low insertion force. Thus, the seal is understood to provide greater seal lip axial deflection than a convention seal having different length to width ratio. The seal is also understood to provide greater seal lip axial deflection than a convention seal having the same inside diameter. In one embodiment, the cross section of the seal is thin at the sealing point and becomes thicker at the base of the seal lip to tailor its stiffness and insertion force. In one embodiment, undercuts are formed proximally and distally of the seal lip. In one example, the undercuts are symmetrical about the seal lip. Optionally, they are not symmetrical. Further, it is understood that since the seal lip deflects axially, there is a component of radial compression due to the bending. Thus, in one aspect of the present invention, a seal lip is provided which deflects axially and has a greater radial compression along an inner radius away from a direction of a lead insertion than an outer radius. Stated differently, the seal lip has a first side surface and a second side surface, and wherein the first side surface has a greater compression than the second side surface when the seal lip deflects axially.

FIG. 3 is an enlarged segmented view of one of the seals 12 of FIG. 1. The seal 12 has a seal lip 24 that deflects mostly radially 26 when the lead 14 is forced through the inside diameter of the seal lip 24. The radial deflection is caused primarily by the relative diameters or dimensions of the lead and the lip seal inside diameter, which is smaller than the lead diameter typically in the order of about 0.01 inch. Although there may be some small amount of axial deflection 28 along the arrow, the degree of axial deflection, as measured in percentage, is smaller than the radial deflection 26.

Figure 4:
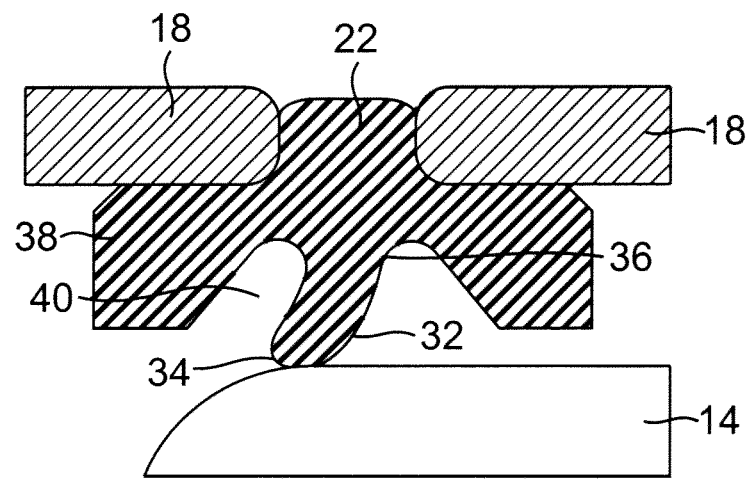
FIG. 4 is an enlarged sectional view of the connector of FIG. 2.

FIG. 4 is an enlarged segmented view of one of the seals 22 of FIG. 2. As shown, the seal lip 32 has a slenderness ratio of about 2 to 1 or greater to achieve the desired low insertion force. For example, the seal lip may have a ratio of 2.1 to 2.6 length to 1 width. The ratio is understood to be length measured from the tip 34 to the base 36 versus the width of the seal lip. Thus, it is understood that a seal 22 provided in accordance with aspects of the present invention includes two end openings and a radial wall 38 extending therebetween. Wherein the interior surface of the radial wall is undulating and comprises a recessed wall surface 40 adjacent a base 36 of a seal lip 32 that is recessed radially outwardly further than an interior wall surface closer to one or both end openings. Said differently, because the seal lip deflects axially, the surface in the direction of deflection has a smaller arc or curvature than that of the opposing surface. Another aspect of the present invention is a provision for deflecting a seal lip a greater axial amount than convention seal lip for purposes of decreasing insertion force. In a further aspect of the present invention, a seal is provided with a seal lip structured to have decreased radial compression and increased axial deflection.

Given the typical contact to lead dimensions, a preferred way to increase the slenderness ratio of the seal lip is to incorporate a seal cross section cut-back. In a less preferred embodiment, both a seal cross section cut-back and an increase seal lip length radially inwardly are provided. The IPG Connector Seal can have one or more sealing lips as required by the application requirements. For example, a seal may have two sealing lips located between two end openings and wherein the interior surface is undulating to provide a recessed interior wall surface.

In another aspect of the present invention, a method is provided for decreasing the insertion force of a lead into an in-line header connector. In one embodiment, the method is provided by forming an in-line header connector comprising a plurality of alternating seals and contact elements and a common bore, and inserting a lead into the common bore with reduced insertion force. Wherein the insertion step is provided by deflecting a plurality of seal lips axially in the direction of insertion of the lead. In another embodiment, the insertion step with reduced insertion force is provided by lengthening the length of at least one seal lip by forming a seal cross section cut-back. In another embodiment, the length of each seal lip for each of the seals in the in-line header connector is lengthened. In a most preferred embodiment, the in-line header connector is connected to an implantable device can.

Figure 5:
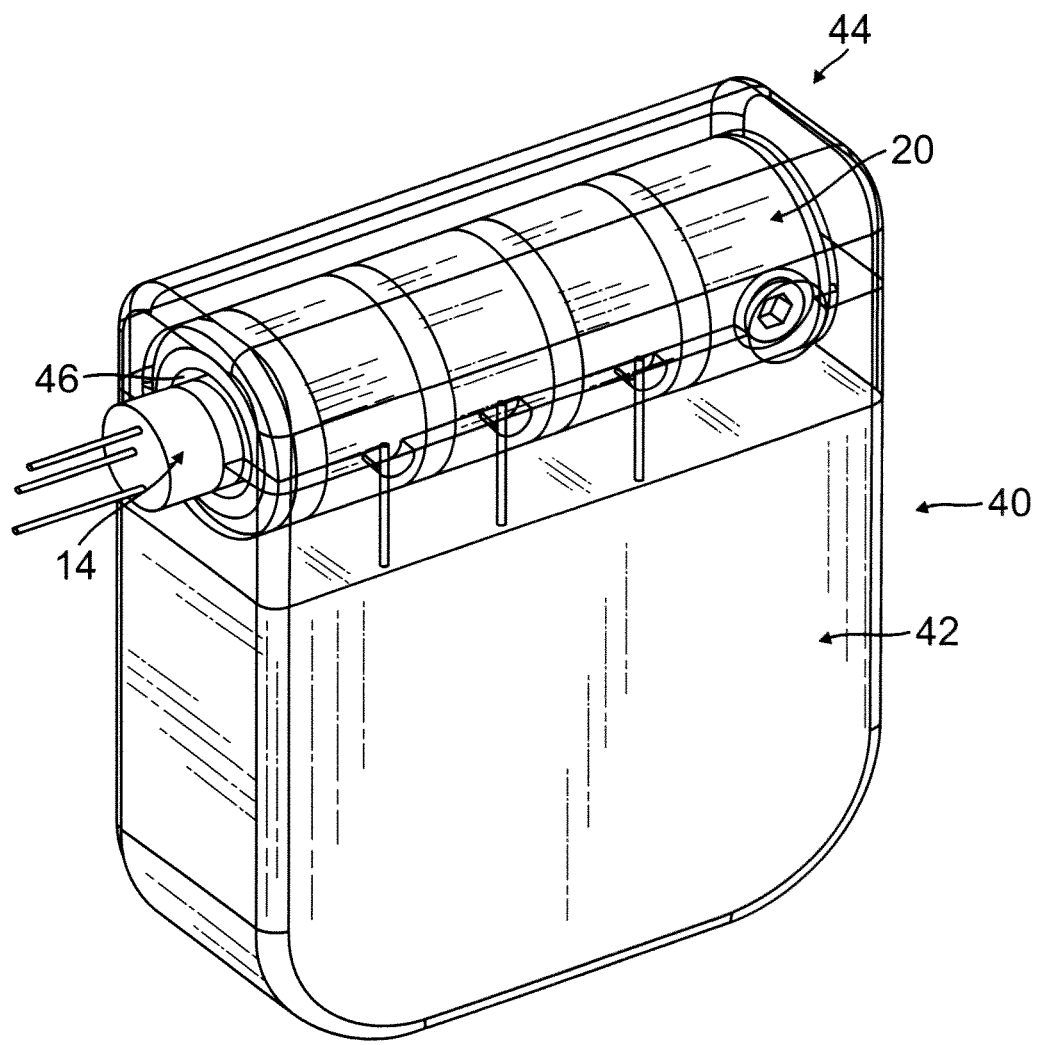
FIG. 5 is an isometric view of an implantable medical device comprising an in-line connector header and a sealed can and having a lead disposed in a common bore of the in-line connector.

FIG. 5 is an isometric view of an implantable medical device 40 provided in accordance with aspects of the present invention. The device 40 comprises a sealed can 42 and a header 44 having the in-line connector 20 disposed therein. The in-line connector comprises a common bore 46 having the lead 14 disposed therein for providing electrical communication between the electronics located inside the sealed can 42 and the electrodes at the other end of the lead (not shown).

Although limited embodiments of the in-line connector and their components have been specifically described and illustrated herein, many modifications and variations will be apparent to those skilled in the art. For example, the seals having a desired length to width ratio for decreasing insertion force may be incorporated in any of the in-line header connectors disclosed in Ser. No. 11/839,103; Ser. No. 12/062,895, and Ser. No. 12/100,646, which were previously incorporated by reference. Accordingly, it is to be understood that the in-line connectors and their components constructed according to principles of this invention may be embodied other than as specifically described herein. The invention is also defined in the following claims.

What is claimed is:

1. A seal assembly comprising:
an elastomeric annular seal body comprising a first end opening having a substantially cylindrical inner surface with a first diameter thereat, a second end opening having a substantially cylindrical inner surface with a second diameter thereat, and an interior surface defining a bore connecting the first end opening and the second end opening, and wherein the bore defines a lengthwise axis running axially through a middle of the bore;
an annular sealing lip comprising a first side, a second side, and a tip located between the first side and the second side, the tip defining a reduced section within the bore having an inside diameter that is smaller than the first diameter and the second diameter;
a width of the sealing lip measured from the first side to the second side of the sealing lip;
a shaft extending through the reduced section within the bore, from the first side to the second side of the sealing lip; and
wherein the sealing lip is part of the interior surface and extends in a radial inward direction in the bore;
wherein the bore has a first undercut formed adjacent the first side of the sealing lip inside the bore, the first undercut having a third diameter which is a largest diameter of the first undercut measured orthogonal to the lengthwise axis and is located at a deepest point of the first undercut;
wherein the bore has a second undercut formed adjacent the second side of the sealing lip inside the bore, the second undercut having a fourth diameter which is a largest diameter of the second undercut measured orthogonal to the lengthwise axis and is located at a deepest point of the second undercut;
wherein the first and second undercuts are reliefs formed in the bore and the third and fourth diameters are larger than the first and the second diameters prior to the shaft extending through the reduced section within the bore so as to reduce an insertion force needed to place the shaft through the reduced section by allowing the sealing lip to axially deflect when the shaft is inserted through the reduced section within the bore; and
wherein the first undercut has a depth measured radially from the substantially cylindrical inner surface of the first opening to the deepest point of the first undercut, the second undercut has a depth measured radially from the substantially cylindrical inner surface of the second opening to the deepest point of the second undercut, and a substantial majority of an overall height of the sealing lip, measured radially from a base of the sealing lip at the deepest point of each undercut to the tip of the sealing lip, is defined by the depths of the first and second undercuts.

2. The seal assembly of claim 1, wherein the third and the fourth diameters are equal.

3. The seal assembly of claim 2, wherein the first and second diameters are equal.

4. The seal assembly of claim 1, wherein the sealing lip has a first side surface and a second side surface, and wherein the first side surface has a greater compression than the second side surface when the sealing lip deflects axially.

5. The seal assembly of claim 1, wherein the sealing lip has a smallest inside diameter on the seal body.

6. A seal assembly comprising:
an elastomeric annular seal comprising a seal body having a wall, an exterior surface, an interior surface defining a bore having a lengthwise axis extending between a first end opening and a second end opening and running axially through a middle of the bore, and an annular sealing lip having a tip extending radially inward and defining a reduced section within the bore having a reduced diameter that is less than a diameter of the first end opening at a substantially cylindrical portion thereof and a diameter of the second end opening at a substantially cylindrical portion thereof, the tip of the sealing lip defining a radially innermost portion of the sealing lip which is also a radially innermost portion of the seal body;
a first undercut formed in the bore adjacent a first side of the sealing lip and a second undercut formed in the bore adjacent a second side of the sealing lip, the first and second undercuts forming a varying surface contour of the interior surface defining the bore such that a radial distance measured orthogonally to the lengthwise axis between the tip of the sealing lip and a radially outermost location of the interior surface in the first undercut, in the second undercut, or in both the first and second undercuts is larger than a radial distance measured between the tip of the sealing lip and the interior surface at the substantially cylindrical portion of the first end opening and a radial distance between the tip of the sealing lip and the interior surface the substantially cylindrical portion of at the second end opening; said first and second undercuts forming the varying surface contour prior to the sealing lip contacting a lead so as to reduce an insertion force required to place the lead through the reduced section by allowing the sealing lip to axially deflect when the lead is inserted through the reduced section;
the lead extending through the reduced section within the bore; and
wherein the first undercut has a depth measured radially from the substantially cylindrical portion of the first opening to the deepest point of the first undercut, the second undercut has a depth measured radially from the substantially cylindrical portion of the second opening to the deepest point of the second undercut, and a substantial majority of an overall height of the sealing lip, measured radially from a base of the sealing lip at the deepest point of each undercut to the tip of the sealing lip, is defined by the depths of the first and second undercuts.

7. The seal assembly of claim 6, wherein the sealing lip has a length to width ratio of at least 2:1.

8. The seal assembly of claim 6, wherein the first and second undercuts are symmetrical.

9. The seal assembly of claim 6, wherein a diameter at the first undercut is larger than the diameter of the first end opening and the diameter of the second end opening, and wherein the tip of the sealing lip is curved.

10. The seal assembly of claim 6, wherein the sealing lip has a smallest inside diameter on the seal body.

11. The seal assembly of claim 9, wherein a diameter at the second undercut is larger than the diameter at the first end opening and the diameter at the second end opening.

12. A method for inserting a lead into an in-line header connector of an implantable medical device comprising:
forming an in-line header connector comprising a common bore, a plurality of seals, and a plurality of contact elements; wherein each seal of the plurality of seals comprises an annular seal body comprising an exterior surface, an interior surface defining a bore extending between a first end opening having a substantially cylindrical portion with a first diameter thereat and a second end opening having a substantially cylindrical portion with a second diameter thereat, wherein each seal of the plurality of seals further comprises an annular sealing lip defining a reduced section of the bore that is smaller than the first diameter and the second diameter and having a tip formed in the bore between the first end opening and the second end opening, wherein the bore defines a lengthwise axis running axially through a middle of the bore, wherein the bore has a first undercut on a first side of the sealing lip having a diameter, which is a largest diameter of the first undercut measured orthogonal to the lengthwise axis and is located at a deepest point of the first undercut, the diameter of the first undercut being larger than the first diameter, wherein the bore has a second undercut on a second side of the sealing lip having a diameter, which is a largest diameter of the second undercut measured orthogonal to the lengthwise axis and is located at a deepest point of the second undercut, the diameter of the second undercut being larger than the second diameter, and wherein the first undercut and the second undercut define a varying surface contour within the bore prior to insertion of a lead so as to reduce an insertion force required to place the lead through the reduced section;

inserting the lead into the common bore which comprises the bore of each of the plurality of seals;

wherein the inserting step comprises deflecting the sealing lip of each of the plurality of seals axially in a direction of the insertion of the lead;

wherein, with respect to each individual seal of the plurality of seals, a radial distance measured orthogonally from the lengthwise axis of the bore to the interior surface at the first diameter is smaller than a radial distance measured orthogonally from the lengthwise axis of the bore to the interior surface at the first undercut; and a radial distance measured orthogonally from the lengthwise axis of the bore to the interior surface at the second diameter is smaller than a radial distance measured orthogonally from the lengthwise axis of the bore to the interior surface at the second undercut; and wherein, with respect to each individual seal of the plurality of seals, the first undercut has a death measured radially from the substantially cylindrical portion of the first opening to the deepest point of the first undercut, the second undercut has a depth measured radially from the substantially cylindrical portion of the second opening to the deepest point of the second undercut, and a substantial majority of an overall height of the sealing lip, measured radially from a base of the sealing lip at the deepest point of each undercut to the tip of the sealing lip, is defined by the depths of the first and second undercuts.

13. The method of claim 12, wherein each sealing lip has a length to width ratio of at least 2:1.

14. The method of claim 12, wherein the first diameter and the second diameter of each seal are equal.

15. The method of claim 12, wherein the first and second undercuts of each seal are symmetrical.

16. The method of claim 12, wherein the diameter at the first undercut and the diameter at the second undercut of each seal are equal.

17. The method of claim 16, wherein each sealing lip has a first side surface and a second side surface, and wherein the first side surface each seal has a greater compression than the second side surface of each seal when the sealing lip of each deflects axially.

18. The method of claim 12, further comprising tightening a set screw against the lead.

* * * * *

UNITED STATES PATENT AND TRADEMARK OFFICE
CERTIFICATE OF CORRECTION

Page 1 of 1

PATENT NO. : 9,682,242 B2
APPLICATION NO. : 12/618493
DATED : June 20, 2017
INVENTOR(S) : Farshid Dilmaghanian It is certified that error appears in the above-identified patent and that said Letters Patent is hereby corrected as shown below:

On the Title Page

In Column 2, in "Other Publications", Line 1, delete "Perliminary" and insert -- Preliminary --, therefor.

In the Claims

In Column 8, Line 9, in Claim 12, delete "death" and insert -- depth --, therefor.

Signed and Sealed this
Third Day of October, 2017

Joseph Matal
*Performing the Functions and Duties of the*
*Under Secretary of Commerce for Intellectual Property and*
*Director of the United States Patent and Trademark Office*